(12) United States Patent
Wu et al.

(10) Patent No.: US 6,379,590 B1
(45) Date of Patent: Apr. 30, 2002

(54) METHOD FOR MAKING UNSYMMETRICALLY SUBSTITUTED FLUORENYL COMPOUNDS FOR NONLINEAR OPTICAL APPLICATIONS

(75) Inventors: Chengjiu Wu, Morristown; Jianhui Shan, Highbridge, both of NJ (US)

(73) Assignee: AlliedSignal Inc., Morris Township, NJ (US)

( * ) Notice: Subject to any disclaimer, the term of this patent is extended or adjusted under 35 U.S.C. 154(b) by 0 days.

(21) Appl. No.: 08/348,385

(22) Filed: Dec. 2, 1994

(51) Int. Cl.[7] .................. F21V 9/00; C07D 303/08; C07C 211/00; C07C 321/00
(52) U.S. Cl. .................. 252/582; 549/20; 549/22; 549/35; 549/39; 549/333; 549/341; 549/551; 549/554; 549/561; 549/563; 564/315; 564/323; 560/9; 560/21; 560/22; 560/23; 560/36; 560/37; 560/45; 560/102; 560/141; 558/418; 558/420; 558/423; 558/388; 558/401; 558/414; 558/416; 558/427; 568/28; 568/29; 568/30; 568/31; 568/32; 568/33; 568/34; 568/35; 568/38; 568/39; 568/41; 568/42; 568/44; 568/45; 568/46; 568/47; 568/49; 568/51; 568/52; 568/54; 568/55; 568/56; 568/57; 568/58; 568/61; 568/62; 568/63; 568/64; 568/65; 568/66; 568/67; 568/579; 568/584; 568/630; 568/631; 568/632; 568/633; 568/634
(58) Field of Search .................. 252/582, 589; 549/551, 554, 561, 563, 20, 22, 35, 39, 333, 341; 564/315, 323; 560/9, 21, 22, 23, 36, 37, 45, 102, 141; 558/418, 420, 423, 388, 401, 414, 416, 427; 568/28, 29, 30, 31, 32, 33, 34, 35, 38, 39, 41, 42, 44, 45, 46, 47, 49, 51, 52, 54, 55, 56, 57, 58, 61, 62, 63, 64, 65, 66, 67, 579, 584, 630, 631, 632, 633, 634

(56) References Cited

U.S. PATENT DOCUMENTS

| 3,546,165 A | 12/1970 | Morgan |
| 4,684,678 A | 8/1987 | Schultz et al. |
| 5,176,854 A | 1/1993 | Ito et al. ............ 252/582 |
| 5,354,511 A | * 10/1994 | Wu et al. ............ 252/582 |

FOREIGN PATENT DOCUMENTS

| JP | 2 084 472 A | 3/1990 |
| JP | 4 345 608 A | 12/1992 |
| JP | 5 011 115 A | 1/1993 |

OTHER PUBLICATIONS

Korshak et al., "Cardo Polymers", J. Macromol. Sci.—Rev. Macromol. Chem. C11(1), 45–142 (1974).
Nicoud et al., "Organic SHG Powder Test Data", Nonlinear Optical Properties Of Organic Molecules and Crystals, vol. 2, pp. 221–249 (1987).
Bunnett, J.F., 12 Q. Rev. Chem. Soc. pp. 1–16 (1958).
Miller, J., Aromatic Nucleophilic Substitution, 70–83 (1968).
Terrier, F., Nucleophilic Aromatic Displacement: The Influence of the Nitro Group, pp. 1–20, (1991).
Foss, R.P., et al., 32–3 Polymer Preprints, pp. 76–77 (American Chemical Society 1991).
Feiring, A.E. 7 Jour. Fluorine Chem., pp. 191–203 (1984).

(List continued on next page.)

*Primary Examiner*—Philip Tucker
(74) *Attorney, Agent, or Firm*—Roger H. Criss; Colleen D. Szuch

(57) ABSTRACT

A new method for producing unsymmetrically substituted fluorenyl compounds, one step of which is the preparation of 2,7-disubstituted fluoren-9-one derivatives via the nucleophilic substitution of a compound of the formula D

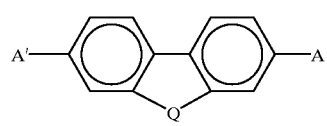

D wherein A' is selected from the group consisting of —Br, —Cl, —F, —NO$_2$, and —CN; A is selected from the group consisting of —NO$_2$, —CN, —CO$_2$R, —C(O)R, —SO$_2$R, —SO$_2$R$_F$, —C(CN)=C(CN)$_2$ and —CH=C(CN)$_2$; R$_F$ is —C$_p$F$_{2p+1}$, p=from about 0 to about 10; R is an straight, branched or cyclic aliphatic alkyl group having about 1 to 10 carbon atoms, or an aromatic group such as phenyl or naphthyl; and

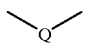

is a carbonyl or a protected carbonyl such as a ketal or thio-ketal such as

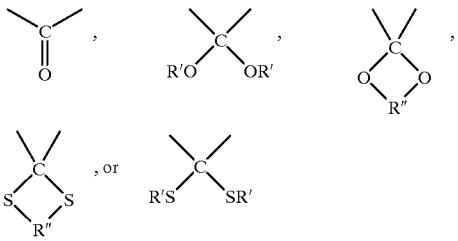

wherein R' is —C$_r$H$_{2r+1}$; R" is —(CH$_2$)$_r$—; and r is independently 2 or 3, with a nucleophilic reagent in the presence of an aprotic solvent. These unsymmetrically substituted fluorenyl compounds can be used as building blocks for making high glass transition temperature polymers for nonlinear optical applications.

2 Claims, No Drawings

OTHER PUBLICATIONS

Sandler, S.R., et al., II Organic Functional Group Preparations, pp. 4–19 (1983).

Sandler, S.R. et al., II(3) Polymer Synthesis pp. 2–5 and 12–61, (1977).

Larock, R.C., Comprehensive Organic Transformations, xiii–xxviii (1989).

Sandler, S.R., et al., III Organic Functional Group Preparations, pp. 1–11, (2nd ed. 1983).

* cited by examiner

METHOD FOR MAKING UNSYMMETRICALLY SUBSTITUTED FLUORENYL COMPOUNDS FOR NONLINEAR OPTICAL APPLICATIONS

CROSS-REFERENCE TO RELATED APPLICATION

This application is related to U.S. patent application Ser. No. 983,065, filed Nov. 27, 1992 (pending, referred as "'065 application"), which is hereby incorporated by reference.

BACKGROUND OF THE INVENTION

1. Field of the Invention

This invention relates to an improved method of making unsymmetrically substituted fluorenyl compounds having strong second order nonlinear optical activities. More specifically, one step of this method further comprises the preparation of unsymmetric 2,7-disubstituted fluorenyl compounds via nucleophilic replacement of at least one of the substituents in a 2,7-disubstituted fluorenyl precursor with another functional group.

2. Prior Art

Organic polymer materials which have large second order nonlinear optical ("NLO") response are of interest for optical applications including data storage, communications, and computing. Important applications include waveguides, interconnects, switches, and the like. The advantages over the conventionally employed inorganic materials, e.g., $LiNbO_4$, in such applications include fast response time, large electro-optical response over a wide frequency range, low dielectric constant, compatibility with silicon wafer technology and others. However, because known NLO active polymers suffer from lack of long term stability under working temperature conditions, their practical utility is limited.

In our '065 Application, we have described thermal stable fluorene-based compounds which are highly NLO active through their unsymmetrical substitution at the aromatic rings of the general formula A:

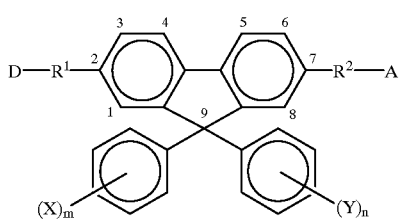

A wherein
  m and n are independently integers of from 1 to 4;
  $R^1$ and $R^2$ which are the same or different in groups $D-R^1-$ and $A-R^2-$, each are optionally present and independently $-Ar-$, $-Ar-H=CH-$ or $-Ar-C\equiv C-$, where in Ar is a divalent bridging group selected from the group consisting of phenylene, biphenylene, naphthalene, and thienylene;
  A is an electron accepting group selected from $-NO_2$, $-CN$, $-CO_2R$, $-C(O)R$, $-SO_2R$, $-SO_2R_F$, $-C(CN)=C(CN)_2$ or $-CH=C(CN)_2$;
  $R_F$ is $-C_pF_{2p+1}$;
  p is an integer of from 1 to 10;
  R is an straight, branched or cyclic aliphatic alkyl group having about 1 to 10 carbon atoms, or an aromatic group such as phenyl or naphthyl;

is an electron donating group selected from $-NH_2$, $-NHR$, $-NR_2$, $-OH$, $-OR$, $-SH$, or $-SR$, wherein R is same as defined above;
  X and Y are groups capable of partaking in polymerizations reactions and are independently selected from the group consisting of $-H$, $-NH_2$, $-NHR$, $-NR_2$, $-OH$, $-OR$, $-SH$, $-SR$, $-COOH$, $-NCO$,

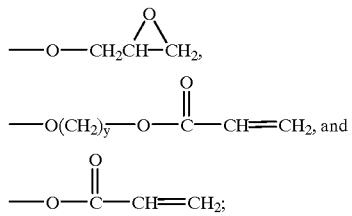

wherein
  R is same as defined above, and
  y is an integer from about 1 to about 10.

As used throughout, the terms m, n, $R^1$, $R^2$, A, $R_F$, p, R, D, y, X and Y are defined as described above in connection with the compounds of formula A unless otherwise indicated.

These unsymmetrically substituted fluorenyl compounds can be used to make high glass transition temperature nonlinear optical polymers. By "unsymmetrical", it is meant that substituents on the two opposite phenyl rings of the fluorenyl moiety are non-identical. Some of these fluorenyl compounds can be grown into non-centrosymmetric crystals, while all of such compounds can be used as additives in host-guest polymer systems.

In U.S. patent application Ser. No. 028,921, filed Mar. 8, 1993, (pending), we have disclosed various polymers exhibiting nonlinear optical properties and high glass transition temperatures made from either the unsymmetrically substituted fluorenyl compounds or monomers described above.

In the simple case wherein both $R^1$ and $R^2$ are not present, formula A may be rewritten as indicated below in formula B:

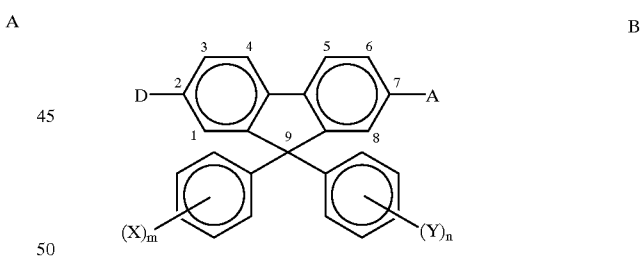

B

These unsymmetrically substituted fluorenyl compounds of the formula B are usually prepared from a 2,7-disubstituted fluorene derivative, preferably a 2,7-disubstituted 9-fluorenone derivative such as 2-fluoro-7-nitro-fluoren-9-one and the easily available 2,7-dinitrofluoren-9-one or its ketal, 2-(2,7-dinitro-9-fluorenyl) 1,3-dioxolane. However, the replacement of a nitro group on these molecules by other functional groups is usually a low-yield, time-consuming, multi-step process which includes the reduction of the nitro group to an amine group followed by subsequent reactions. See, e.g., '065 application, "Step 2".

A nitro group has long been known to activate another functional group in the same aromatic moiety towards nucleophilic displacements ("SNAr reactions"). See, e.g., Bunnett, J. F., 12 Q. Rev. Chem. Soc. 1 (1958); Miller, J., Aromatic Nucleophilic Substitution, (1968); and Terrier, F., Nucleophilic Aromatic Displacement: The Influence of the Nitro Group, (1991). In all three of these references, the activation of the nitro group is localized in the same aromatic ring containing the substituent group. By contrast, examples in which the transmission of nitro activation in one ring to another ring attached thereto are rare, if any. To our knowledge, there is no successful example of nucleophilic replacement of a substituent on one ring of a biphenyl or fluorenyl molecule activated by a nitro group attached on the opposite ring.

It would be desirable to provide an improved method for preparing these unsymmetric substituted fluorenyl compounds of general formula B in high yield, wherein the method would involve only a minimal amount of steps.

SUMMARY OF THE INVENTION

In accordance with this invention, there is provided a method for preparing unsymmetrical 2,7-disubstituted fluoren-9-one derivatives, said method comprising:

reacting a compound of the formula D:

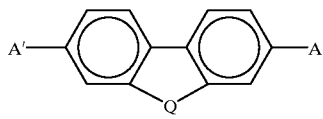

D wherein
A' is the same as or different from A, and is a leaving group selected from the group consisting of —Br, —Cl, —F, —NO$_2$, and —CN;

is a carbonyl or a protected carbonyl, wherein said protected carbonyl is a ketal or thio-ketal selected from the group consisting of

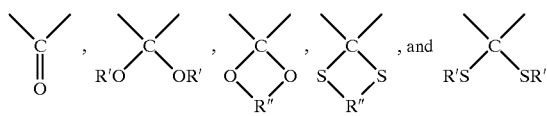

wherein
R' is —C$_r$H$_{2r+1}$;
R'' is —(CH$_2$)$_r$; and
r is independently an integer of 2 or 3;
A is an electron accepting group selected from the group consisting of NO$_2$, —CN, —CO$_2$R, —C(O)R, —SO$_2$R, —SO$_2$R$_F$, —C(CN)=C(CN)$_2$ and —CH=C(CN)$_2$;
R$_F$ is —C$_p$F$_{2p+1}$;
p is an integer of from about 1 to about 10;
R is selected from the group consisting of phenyl, napthyl, and a straight, branched and cyclic aliphatic alkyl group having from about 1 to about 10 carbon atoms;

with a nucleophilic reagent in the presence of an aprotic solvent and under conditions sufficient to form a compound of the formula C

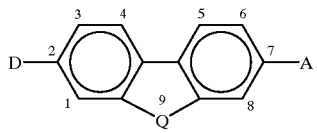

C wherein

A is as previously defined in formula D;

D is an electron donating group selected from the group consisting of —NH$_2$, —NHR, —NR$_2$, —OH, —OR, —SH, and —SR;

R is as previously defined in set A of formula D; and

is as previously defined in formula D.

Another aspect of this invention is directed to an improved process for producing unsymmetrically substituted fluorenyl compounds, said process comprising a) reacting a compound of the formula D'

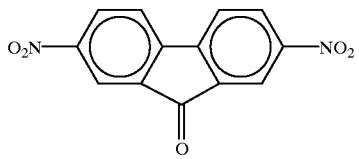

D' with a protection reagent selected from the group consisting of (CH$_2$OH)$_2$,

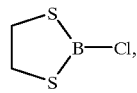

and (CH$_3$O)$_3$CH in the presence of an acid catalyst and a solvent under conditions sufficient to produce a protected carbonyl compound of the formula E:

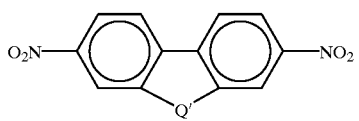

E wherein

is

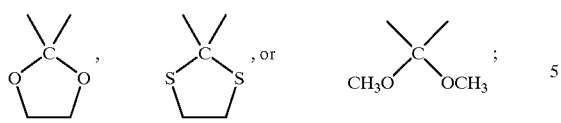

b) reacting said protected carbonyl compound with a nucleophilic reagent in an aprotic solvent and under conditions sufficient to produce a protected 2,7-disubstituted fluoren-9-one derivative thereof of the formula F:

   F wherein
D is selected from the group consisting of —NH$_2$, —NHR, —NR$_2$, —OH, —OR, —SH, and —SR;
R is selected from the group consisting of phenyl, naphthyl, and a straight, branched and cyclic aliphatic alkyl group having from about 1 to about 10 carbon atoms; and

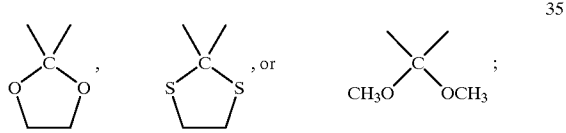

is

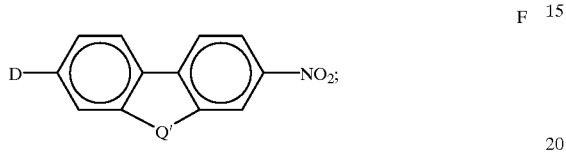

c) deprotecting said 9-carbonyl of said 2,7-disubstituted fluoren-9-one derivative in the presence of both the acid catalyst of step a and active aromatic compounds under conditions sufficient to yield a 2,7-disubstituted fluorenyl compound geminately alkylated at a 9-carbon, as shown in the formula G:

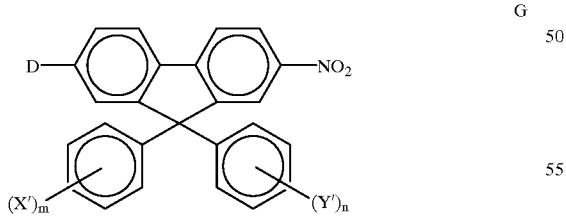   G wherein
m and n are independently from about 1 to about 4;
X' and Y' are independently selected from the group consisting of H, —NH$_2$, —NR$_2$, —NHR, —OH, —SR, —OR and —SH;
R is as previously defined in set D of formula F;
D is selected from the group consisting of —NH$_2$, —NHR, —NR$_2$, —OH, —OR, —SH, and —SR;
R is as previously defined in set D of formula F; and d) optionally alkylating the compound of formula G to form a compound having formula H:

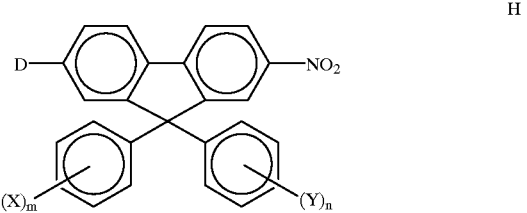   H wherein
D is as previously defined in formula F;
m and n are independently from about 1 to about 4; and
X and Y are independently selected from the group consisting of —H, —NH$_2$, —NHR, —NR$_2$, —OH, —OR, —SH, —SR, —COOH, —NCO,

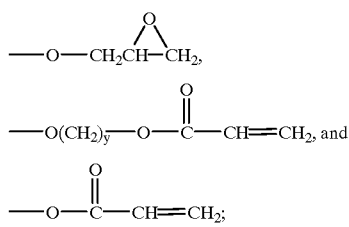

wherein
R is as previously defined in set D of formula F; and
y is an integer from about 1 to about 10;

in order to obtain an unsymmetrically substituted fluorenyl compound having formula H having at least one X or Y group selected from the group consisting of —COOH, —NCO,

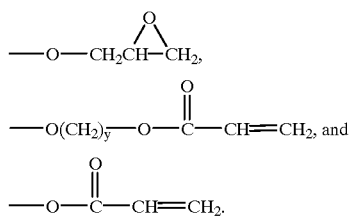

Yet another aspect of this invention is directed to a process for producing unsymmetrically substituted fluorenyl compounds having the formula Z

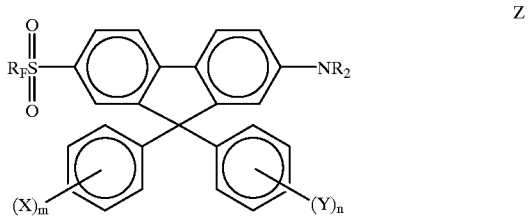   Z said process comprising:

a) reacting a compound of the formula D'

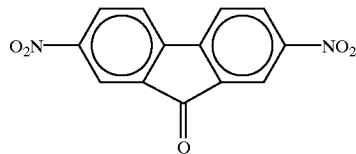

with a protection reagent selected from the group consisting of $(CH_2OH)_2$,

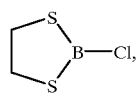

and $(CH_3O)_3CH$ in the presence of an acid catalyst and a solvent under conditions sufficient to produce a protected carbonyl compound of the formula E:

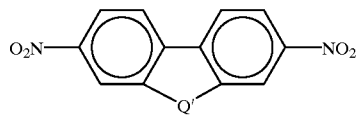

wherein

is

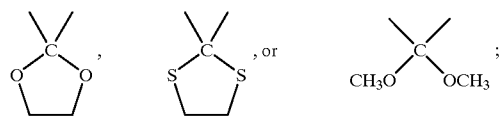

b) reacting said protected carbonyl compound with a nucleophilic reagent in an aprotic solvent and under conditions sufficient to produce a protected 2,7-disubstituted fluoren-9-one derivative thereof of the formula F':

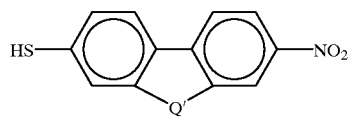

wherein

is

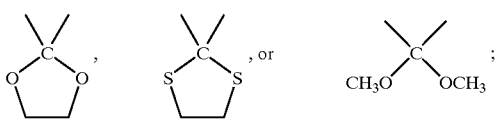

c) substantially fluoroalkylating said compound having formula F' with a reagent of formula $R_FI$ to form a fluoroalkyl sulfide derivative having formula L';

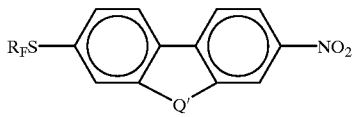

wherein
$R_F$ is $—C_pF_{2p+1}$;
p is an integer of from about 1 to about 10; and

is as previously defined in formula F';

d) substantially oxidizing said fluoroalkyl sulfide of step c with an oxidizing reagent to form a fluoroalkyl sulfone derivative having formula K';

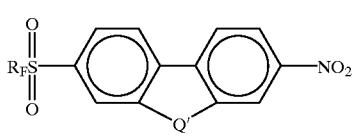

wherein $R_F$, p, and

are is as defined in Formula L';

e) further reacting the fluoroalkyl sulfone derivative of step d with a nucleophilic reagent in the presence of an aprotic solvent to form a compound having formula M'

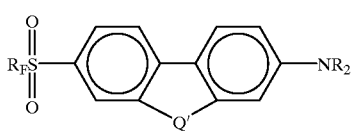

wherein
$R_F$, p, and

is as defined in Formula L', and
R is selected from the group consisting of phenyl, naphthyl, and a straight, branched and cyclic aliphatic alkyl group having from about 1 to about 10 carbon atoms;
said compound having formula M' having a 9-carbonyl;

f) deprotecting said 9-carbonyl of said 2,7-disubstituted fluoren-9-one derivative of step e in the presence of the acid catalyst of step a and active aromatic compounds and under conditions sufficient to yield a 2,7-disubstituted fluorenyl compound geminately alkylated at the 9-carbon, as shown in the formula G'

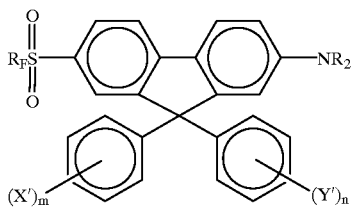

G' wherein
m and n are independently from about 1 to about 4;
X' and Y' are independently selected from the group consisting of H, —NH$_2$, —NR$_2$, —NHR, —OH, —SR, —OR and —SH;
R is as previously defined in formula M';
R$_F$ and p are as defined in formula L'; and g) optionally alkylating the compound having formula G' to form a compound having formula H':

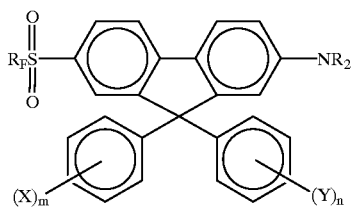

H' wherein
R$_F$ and p are as defined in formula L';
m and n are independently from about 1 to about 4;
R is as previously defined in formula M'; and
X and Y are groups capable of partaking in polymerization reactions and are independently selected from the group consisting of —H, —NH$_2$, —NHR, —NR$_2$, —OH, —OR, —SH, —SR, —CO$_2$H, —NCO,

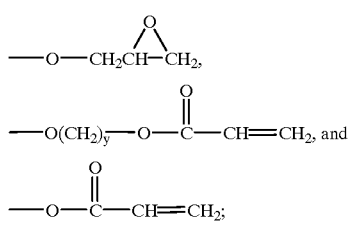

wherein
y is about 1 to about 10;
in order to obtain an unsymmetrically substituted fluorenyl compound having at least one X or Y group selected from the group consisting of —COOH, —NCO,

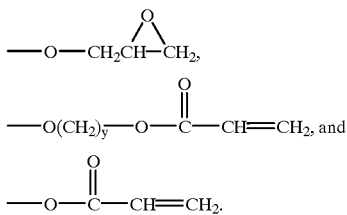

The above-mentioned nucleophilic substitution method for producing unsymmetrical 2,7-disubstituted fluoren-9-one derivatives is not only simpler and faster than the previously known methods for doing the same, but it also results in higher product yields. In addition, the cycle time for producing unsymmetrically substituted fluorenyl compounds is also reduced since the second step in its known method of production, see, e.g., '065 application, may be replaced with the one-step nucleophilic substitution of the present invention.

DESCRIPTION OF THE PREFERRED EMBODIMENTS

One aspect of this invention relates to the improved method for preparing unsymmetrical 2,7-disubstituted fluoren-9-one derivatives. In this method, the leaving group A' in a 2,7-disubstituted fluoren-9-one derivative having formula D is replaced by a nucleophile group, D, as represented by the following general scheme:

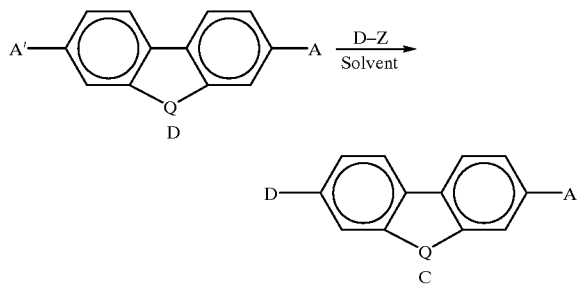

In the above scheme, A' is a leaving group selected from the group consisting of but not limited to —Br, —Cl, —F, —NO$_2$, and —CN. Preferred leaving groups include —F or —NO$_2$, with —NO$_2$ being the most preferred.

A is a strong electron accepting group which activates the nucleophilic replacement and includes, but is not limited to —NO$_2$, —CN, —CO$_2$R, —C(O)R, —SO$_2$R, —SO$_2$R$_F$, —C(CN)=C(CN)$_2$ and —CH=C(CN)$_2$, wherein R$_F$ is —C$_p$F$_{2p+1}$,
p is an integer of from about 1 to about 10, preferably about 1 to about 3; and
R is an aromatic group, such as phenyl or napthyl, or a straight, branched or cyclic a aliphatic alkyl group having from about 1 to about 10 carbon atoms.

Preferred electron accepting groups include —CN, —SO$_2$R, —SO$_2$R$_F$ and —NO$_2$, with —NO$_2$ being most preferred.

is a carbonyl or a protected carbonyl such as a ketal or thio-ketal selected from the group consisting of:

 , 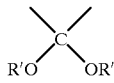 , 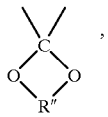 ,

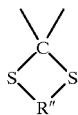 , and 

wherein

R' is —C$_r$H$_{2r+1}$;

R" is —(CH$_2$)$_r$; and r is independently an integer of 2 or 3.

Preferably,

is a ketal, with a 1,3-dioxolane being most preferred.

Suitable nucleophilic reagents are of the formula D—Z, wherein the D moiety is an electron donating group including, but are not limited to, —NH$_2$, —NHR, —NR$_2$, —OH, —OR, —SH, and —SR. The Z moiety is a metal cation. Preferred D moieties include —NR$_2$, —SH, and —OR, with —NR$_2$ and —OR being most preferred. Preferred Z moieties include lithium, sodium and potassium.

The molar ratio of compounds of formula D to nucleophilic reagents of formula D—Z is about 1:1–10, and preferably about 1:1.5–5.

In order to facilitate the substitution reaction, aprotic solvents may be used. Suitable solvents include, but are not limited to, diglyme, dimethyl-formamide, dimethylacetamide, N-methylpyrrolidone, and dimethylsulfoxide, with dimethylformamide ("DMF") being preferred.

The substitution reaction of this invention is not limited to the replacement of only one leaving group, such as the A' moiety, in compounds having formula D. Rather, both the A and A' group in the precursor compound D may sequentially replaced according to the following brief scheme. This is accomplished by first converting the D group of formula C, which was obtained from the first replacement reaction into an electron acceptor group A", followed by replacing the remaining A group by the same nucleophilic mechanism.

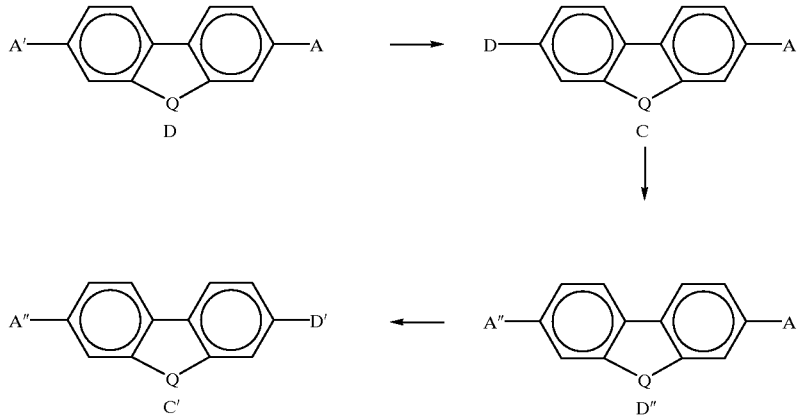

wherein

A" is an electron accepting, weak leaving group selected from —CN, —CO$_2$R, —C(O)R, —SO$_2$R, —SO$_2$R$_F$, —C(CN)=C(CN)$_2$ and —CH=C(CN)$_2$;

R and R$_F$ are as previously defined in formula D, and

D has the same definition as D in formula F.

One such transformation is exemplified in the following reaction scheme in which the D' in Formula M is —N$_2$R and A" is —SO$_2$R$_F$:

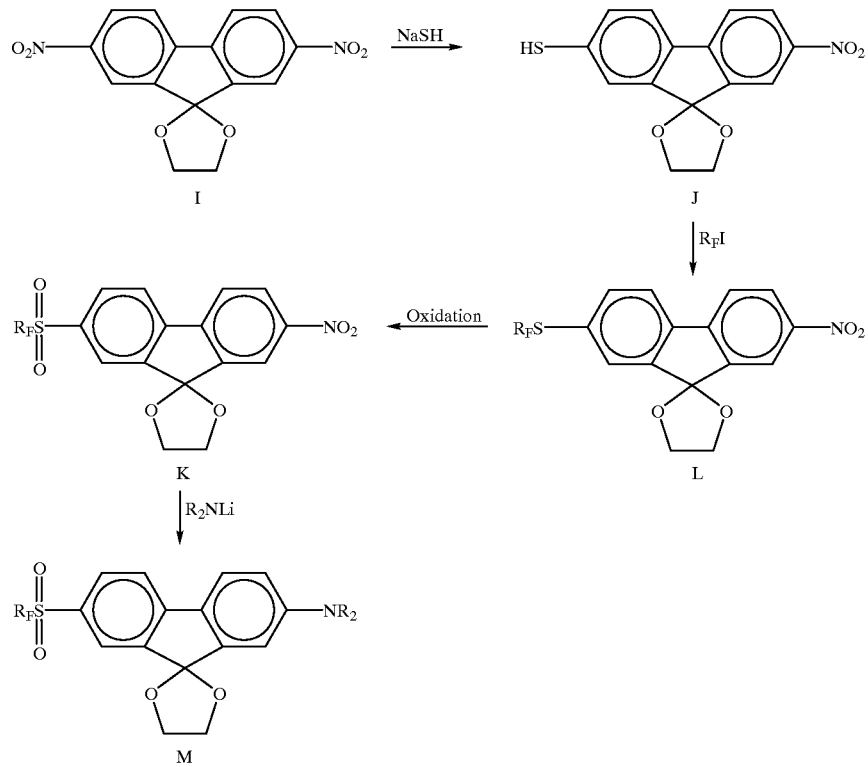

The compounds having formulas J and L, respectively, are substantially fluoroalkylated and substantially oxidized, respectively. By "substantially fluoroalkylated", it is meant that the —SH group of at least one of the compounds having formula J is fluoroalkylated. By "substantially oxidized", it is meant that the —SR$_F$ group of at least one compound having formula L is oxidized. Details of fluoroalkylation by R$_F$I on the sulfur atom and subsequent oxidation to a fluoroalkylsulfonyl is well documented in literature. See, e.g., Foss, R. P., et al., 32–3 Polymer Preprints 76 (American Chemical Society 1991); Feiring, A. E. 7 Jour. Fluorine Chem. 191 (1984).

The starting material for the substitution reaction, i.e. compounds having formula D, may be synthesized by methods well known in the art. See, e.g., '065 Application; Step I infra. All solvents and nucleophilic reagents used in the substitution reactions are commercially available or, in the alternative, may be synthesized by well known methods. Both reagents having the formula, R$_F$I, as well as the oxidation reagents, such as H$_2$O$_2$, Na$_2$O$_2$, CrO$_3$, and the like, are commercially available.

The substitution reaction may be conducted in any conventional reactor at atmospheric pressure.

The temperature at which the substitution reaction is conducted and the period of reaction will depend on the starting material, solvent, and reactant selected. One of ordinary skill in the art can readily optimize the conditions of the reaction without undue experimentation to get the claimed results, but the temperature will generally be in the range of from about 25° C. to about 100° C., and preferably about 25° C. to about 50° C., for about 1 to about 24 hours, and preferably from about 1 to about 6 hours.

Another aspect of this invention is directed to a three step process for preparing compounds of formula B":

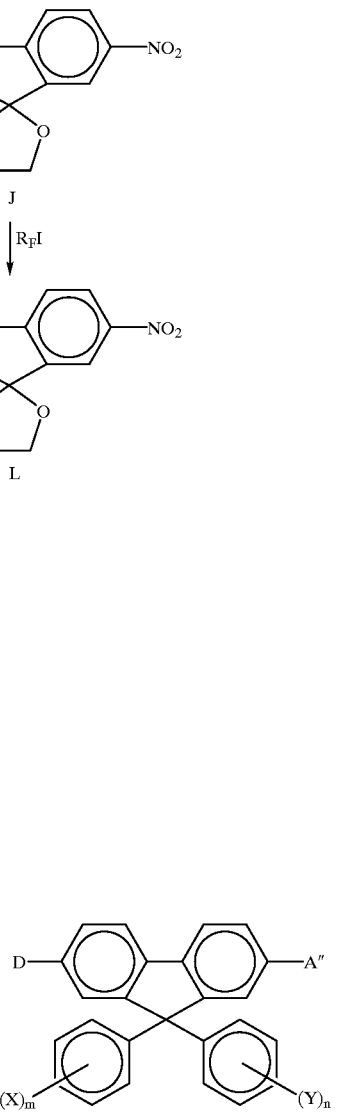

wherein

A" is an electron accepting, weak leaving group selected from —CN, —CO$_2$R, —C(O)R, —SO$_2$R, —SO$_2$R$_F$, —C(CN)=C(CN)$_2$ and —CH=C(CN)$_2$; and R and R$_F$ are as previously defined in Formula D.

The first step involves protecting the 9-carbonyl groups of the starting fluorenone derivative, which may be a compound of the formula D'

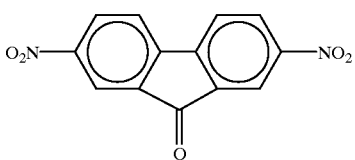

D'

The protection reaction involves the reaction of a compound having formula D' with a protection reagent in the presence of an acid catalyst and a solvent under conditions sufficient to produce a protected carbonyl compound of the formula E:

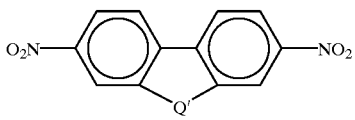

E wherein

is

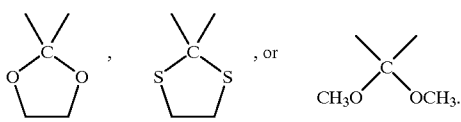

Suitable protective reactants may be selected from the group consisting of $(CH_2OH)_2$,

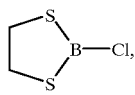

and $(CH_3O)_3CH$, with $(CH_2OH)_2$ being most preferred.

The starting material for the protection reaction, i.e. compounds of formula D', and the reagent are both available from commercial sources. In the protection reaction, the molar ratio of compounds of formula D' to the protection reagent is about 1:2–20, preferably about 1:5–10.

Suitable acid catalysts may be selected from the group consisting of hydrogen chloride, hydrogen bromide, sulfuric acid, phosphoric acid, p-toluenesulfonic acid, trifluoromethanesulfonic acid, and fluorosulfonic acid with p-toluenesulfonic acid being preferred. The amount of catalyst used in the protection reaction is, based upon the total moles of the compound having formula D', from about 0.001% to about 10%, and preferably about 0.01% to about 1%.

In order to facilitate the protection reaction, a commercially available solvent such as chlorobenzene, dichlorobenzene, and xylene is used. Chlorobenzene is preferred.

The protection reaction may be conducted in any conventional reactor at atmospheric pressure.

The temperature at which the protection reaction is conducted and the period of reaction will depend on the species and amount of starting material, catalyst, solvent, and protective reactant selected. One of ordinary skill in the art can readily optimize the conditions of the reaction without undue experimentation to get the claimed results, but the temperature will generally be in the range of from about 100° C. to about 200° C., and preferably at the boiling point of the selected solvent, for about 16 to about 100 hours, and preferably from about 24 to about 48 hours.

In the second step, the protected carbonyl compound of formula E:

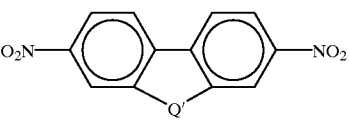

E is reacted with a nucleophilic reagent in an aprotic solvent to produce an protected 2,7-disubstituted fluoren-9-one derivative having formula F

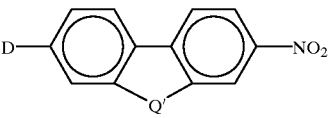

F wherein

is

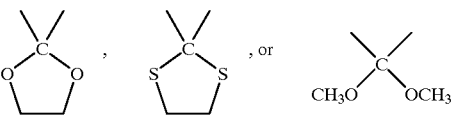

D is an electron donating group selected from the group consisting of $-NH_2$, $-NHR$, $-NR_2$, $-OH$, $-OR$, $-SH$, and $-SR$.

In an alternative embodiment, both $-NO_2$ groups in the precursor compound having formula E may be replaced via the mechanism as exemplified in the following scheme:

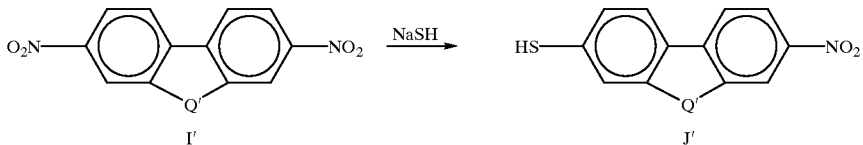

-continued

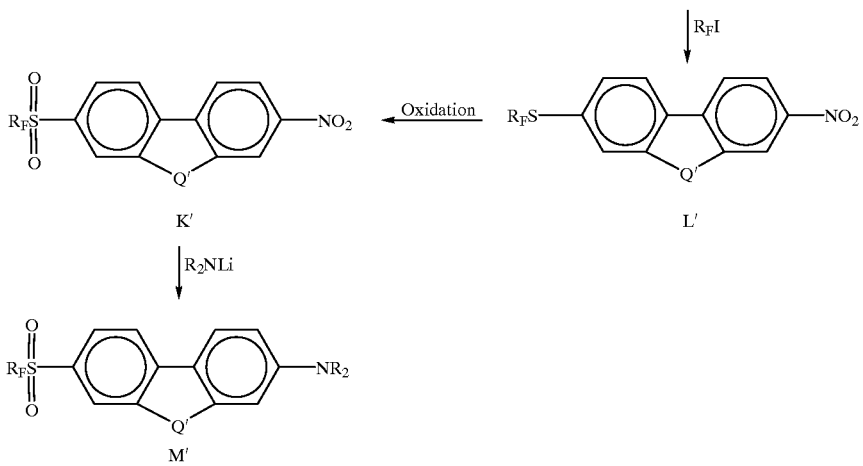

K'      L'

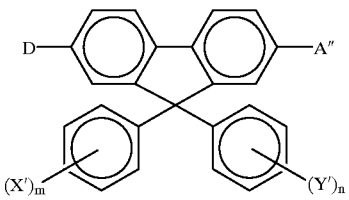

M'

The compounds having formulas J' and L', respectively, are substantially fluoroalkylated and substantially oxidized, respectively. By "substantially fluoroalkylated", it is meant that the —SH group of at least one of the compounds having formula J' is fluoroalkylated. By "substantially oxidized", it is meant that the —SR$_F$ group of at least one compound having formula L' is oxidized. Any of the aforementioned oxidation reagents are suitable.

The third step involves deprotection and simultaneous alkylation of the 9-carbonyl group of compounds of formula F or M' with active aromatic compounds in the presence of an acid catalyst to yield a 2,7-disubstituted fluorenyl compound geminately alkylated at the 9-carbon having formula G":

G"

wherein
said acid catalyst is of the formula HX" and said aromatic compounds are of the formula $C_6H_5'$, or $C_6H_5Y'$, wherein A" can be, but is not limited to an electron accepting, weak leaving group selected from —CN, —NO$_2$, —CO$_2$R, —C(O)R, —SO$_2$R, —SO$_2$R$_F$, —C(CN)=C(CN)$_2$ and —CH=C(CN)$_2$; and R and R$_F$ are as previously defined in Formula D;

HX" is a strong acid such as HCl, HBr, H$_2$SO$_4$, H$_3$PO$_4$, p-toluenesulfonic acid, fluorosulfonic acid; or trifluoromethyl-sulfonic acid; and X' and Y' are independently selected from the group consisting of —H, —NR$_2$, —OR, —SR, —NH$_2$, —NHR, —SH, —OH;
R is selected from the group consisting of phenyl, naphthyl, and a straight, branched and cyclic aliphatic alkyl group having from about 1 to about 10 carbon atoms;
m and n are independently from about 1 to about 4; and
D is an electron donating group selected from the group consisting of —NH$_2$, —NHR, —NR$_2$, —OH, —OR, —SH, and —SR.

Active aromatic compounds such as phenol, aniline, and monoalkylaniline, are preferred. These active aromatic compounds also serve as solvents for the deprotection reaction. The mole ratio of the compound having formula F or M' to the aromatic compound, i.e. phenol, required for the deprotection reaction is about 1:2–20, and preferably about 1:5–10.

Preferable acid catalysts useful in the deprotection reaction include p-toluenesulfonic acid and trifluoromethanesulfonic acid. Although the amount of acid catalyst used may vary widely, it is recommended that about 0.1% to about 10%, and preferably 1% to about 5%, based upon the moles of the starting material used for the deprotection reaction, i.e. the compound having either formula F or M', is used.

The aromatic compounds and acid catalysts used in the deprotection reaction are commercially available.

The deprotection and alkylation reaction may be conducted in any conventional reactor at atmospheric pressure.

The temperature at which the deprotection reaction is conducted and the period of reaction will depend on the starting material, i.e. compound having formula F or M', acid catalyst, and aromatic compound reactant selected. One of ordinary skill in the art can readily optimize the conditions of the reaction without undue experimentation to get the claimed results, but the temperature will generally be in the range of from about 50° C. to about 150° C., and preferably about 50° C. to about 100° C., for about 2 to about 24 hours, and preferably from about 6 to about 12 hours.

In order to obtain compounds having formula H" wherein the X or Y groups are other than the X' or Y' groups provided in formula G", it is necessary to functionally transform the compound having formula G" into a compound having formula H"

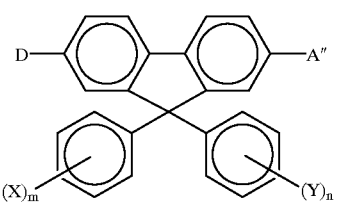

wherein
- A" can be, but is not limited to an electron accepting, weak leaving group selected from —CN, —NO$_2$, —CO$_2$R, —C(O)R, —SO$_2$R, —SO$_2$R$_F$, —C(CN)=C(CN)$_2$ and —CH=C(CN)$_2$; and
  R and R$_F$ are as previously defined in Formula D;
- D is an electron donating group selected from the group consisting of —NH$_2$, —HR, —NR$_2$, —OH, —OR, —SH, and —SR;
- X and Y are independently selected from the group consisting of —H, —NH$_2$, —NHR, —NR$_2$, —OH, —OR, —SH, —SR, —COOH, —NCO,

—O—CH$_2$CH—CH$_2$,
   \O/

—O(CH$_2$)$_y$—O—C(=O)—CH=CH$_2$, and

—O—C(=O)—CH=CH$_2$;

m and n are independently from about 1 to about 4; and
y is an integer from about 1 to about 10.

via a conventional alkylation procedure. Such conventional alkylation procedures are well known in the literature. See, e.g., Sandler, S. R., et al., H(5, 9, 10, 17) and III(5) Organic Functional Group Preparations (2nd ed 1983); Sandler, S. R. et al., II(3) Polymer Syntheses (1977); Larcock, R. C., Comprehensive Organic Transformations, (1989).

EXAMPLES

Example 1

Preparation of 2-(2-methoxy-7-nitro-9-fluorenyl)-1,3-dioxolane

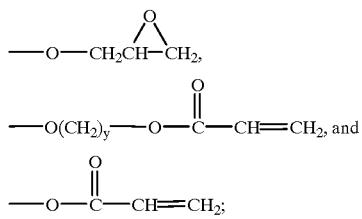

For a period of two hours, 8 parts of sodium methoxide was added to a solution of 10 parts of 2-(2,7-dinitro-9-fluorenyl)-1,3-dioxolane in 300 parts of dimethylformamide contained within a 5 liter flask at room temperature. The mixture was magnetically stirred for 20 hours. All of the mixture was then diluted with 1800 parts of water. A yellow solid was precipitated therefrom, collected on a filter, washed with water and dried under vacuum. The dried filtered product was further purified in a chromatography column packed with silica gel (Merck Grade 60) and developed by methylene chloride to provide 8.2 parts of product (86% yield).

The product, which was characterized by $^1$H and $^{13}$C NMR; had a structure consistent with that assigned and the following properties: $^1$H NMR [d (ppm), No. of H's]: 8.28, 1H; 8.18, 1H; 7.82, 2H; 7.14, 1H; 7.04, 1H; 4.40, 4H; 3.82, 3H. $^{13}$C NMR [d (ppm), No. of C's]: 161.9, 1C; 148.1, 1C; 146.8, 1C; 146.1, 1C; 145.7, 1C; 129.3, 1C; 126.9, 1C; 123.5, 1C; 120.4, 1C; 119.0, 1C; 116.8, 1C; 110.5, 1C; 110.4, 1C; 66.1, 2C; 56.0, 1C.

Example 2

Preparation of 2-(2-mercapto-7-nitro-9-fluorenyl)-1,3-dioxolane

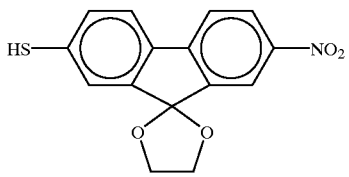

For a period of 0.5 hours, 10 parts of sodium sulfide nonahydrate was added to a solution of 6 parts of 2-(2,7-dinitro-9-fluorenyl)-1,3-dioxolane in 300 parts of dimethylformamide contained within a 1 liter flask at room temperature. The mixture was then stirred for 20 hours, diluted with 1000 parts of methylene chloride, and washed with water in the amount of 4 parts water: 1000 parts methylene chloride.

After the solvent was removed from the washed product via evaporation, the resulting product was further purified in the chromatography column of Example 1 and developed by a 1:4 weight mixture of ethyl acetate and hexane to provide 2.2 parts of product (38% yield).

The product, which was characterized by $^1$H and $^{13}$C NMR; had a structure consistent with that assigned and the following properties: $^1$H NMR [d (ppm), No. of H's]: 8.20, 1H; 8.10, 1H; 7.62, 1H; 7.48, 1H; 6.75, 1H; 6.62, 1H; 5.82, 1H; 4.35, 4H. $^{13}$C NMR [d (ppm), No. of C's] : 152.0, 1C; 148.0, 1C; 147.8, 1C; 145.4, 1C; 144.8, 1C; 127.0, 1C; 124.1, 1C; 123.4, 1C; 118.7, 1C; 118.6, 1C; 115.5, 1C; 110.7, 1C; 109.6, 1C; 65.1, 2C.

Example 3

Preparation of 2-(2-N,N-dimethylamino-7-nitro-9-fluorenyl)-1,3-dioxolane

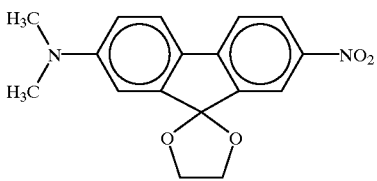

10 parts of 2-(2,7-dinitro-9-fluorenyl)-1,3-dioxolane and 800 parts of dimethylformamide were added to a reaction flask, then magnetically stirred at room temperature until homogeneous. 12.3 parts of lithium dimethylamide was then slowly added to the continuously-stirred homogeneous mixture. After 18 hours of stirring, the mixture was filtered. The filtrate was diluted with 1600 parts methylene chloride and washed with water.

After the solvent was removed by evaporation, the product was further purified in a chromatography column and developed as described in Example 2 to provide 3.5 parts of product (35% yield).

The product, which was characterized by $^1$H and $^{13}$C NMR; had a structure consistent with that assigned and the following properties: $^1$H NMR [d (ppm), No. of H's]: 8.20, 1H; 8.12, 1H; 7.64, 2H; 6.82, 1H; 6.72, 1H; 4.42, 4H; 3.05, 6H. $^{13}$C NMR [d (ppm), No. of C's]: 152.5, 1C; 147.8, 1C; 147.4, 1C; 145.5, 1C; 145.2, 1C; 127.0, 1C; 124.1, 1C; 123.2, 1C; 118.9, 1C; 118.7, 1C; 113.8, 1C; 110.8, 1C; 107.6, 1C; 66.0, 2C, 40.3, 2C.

Example 4

Preparation of 2-(2-ethoxy-7-nitro-9-fluorenyl)-1,3-dioxolane

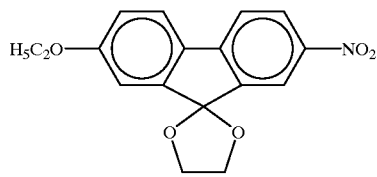

Following the same procedure described in Example 1, from 10 parts of 2-(2,7-dinitro-9-fluorenyl)-1,3-dioxolane and 12.5 parts of potassium ethoxide there was obtained 9 parts of product, its $^1$H and $^{13}$C NMR was consistent with the assigned structure.

Example 5

Preparation of 2-(2-phenoxy-7-nitro-9-fluorenyl)-1,3-dioxolane

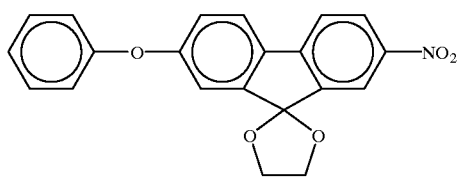

Following the same procedure described in Example 1, from 10 parts of 2-(2,7-dinitro-9-fluorenyl)-1,3-dioxolane and 21 parts of sodium phenoxide there was obtained 12 parts of product, its $^1$H and $^{13}$C NMR was consistent with the assigned structure.

Example 6

Preparation of 2-(2-thiomethoxy-7-nitro-9-fluorenyl)-1,3-dioxolane

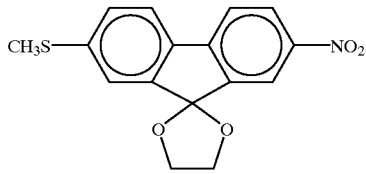

Following the same procedure described in Example 2, from 6 parts of 2-(2,7-dinitro-9-fluorenyl)-1,3-dioxolane and 10 parts of sodium thiomethoxide there was obtained 3 parts of product, its $^1$H and $^{13}$C NMR was consistent with the assigned structure.

Example 7

Preparation of 2-(2-N,N-diethylamino-7-nitro-9-fluorenyl)-1,3-dioxolane

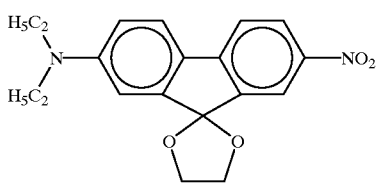

Following the same procedure described in Example 3, from 10 parts of 2-(2,7-dinitro-9-fluorenyl)-1,3-dioxolane and 19 parts of lithium diethylamide there was obtained 3.5 parts of product, its $^1$H and $^{13}$C NMR was consistent with the assigned structure.

Example 8

Preparation of 2-(2-N,N-diphenylamino-7-nitro-9-fluorenyl)-1,3-dioxolane

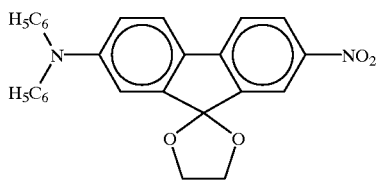

Following the same procedure described in Example 3, from 10 parts of 2-(2,7-dinitro-9-fluorenyl)-1,3-dioxolane and 31 parts of lithium diphenylamide there was obtained 8.5 parts of product, its $^1$H and $^{13}$C NMR was consistent with the assigned structure.

Example 9

Preparation of 2-(2-N-methy-anilino-7-nitro-9-fluorenyl)-1,3dioxolane

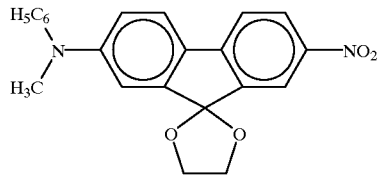

Following the same procedure described in Example 3, from 10 parts of 2-(2,7-dinitro-9-fluorenyl)-1,3-dioxolane and 25 parts of lithium N-methylanilide there was obtained 5.5 parts of product, its $^1$H and $^{13}$C NMR was consistent with the assigned structure.

These Examples demonstrate that a high yield of unsymmetrical 2,7-disubstituted fluoren-9-one derivatives may be prepared according to the claimed process via a minimal amount of steps.

What is claimed is:

1. A process for producing unsymmetrically substituted fluorenyl compounds, said process comprising a) reacting a compound of the formula D'

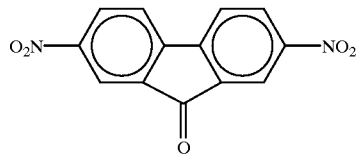

with a protection reagent selected from the group consisting of (CH$_2$OH)$_2$,

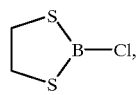

and (CH$_3$O)$_3$CH in the presence of an acid catalyst and a solvent under conditions sufficient to produce a protected carbonyl compound of the formula E:

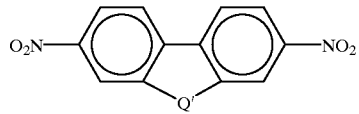

wherein

is

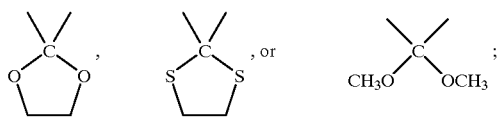

b) reacting said protected carbonyl compound with a nucleophilic reagent of the formula D—Z wherein D is an electron donating group selected from the group consisting of —NH$_2$, —NHR, —NR$_2$, —OH, —OR, —SH, and —SR, and Z is a metal cation, in an aprotic solvent and under conditions sufficient to produce a protected 2,7-disubstituted fluoren-9-one derivative thereof of the formula F':

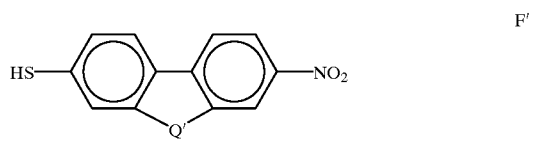

wherein

is

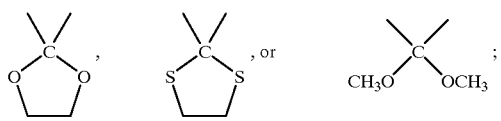

c) substantially fluoroalkylating said compound having formula F' with a reagent of formula R$_F$I to form a fluoroalkyl sulfide derivative having formula L';

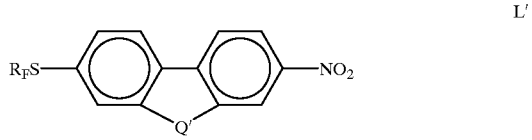

wherein R$_F$ is —C$_p$F$_{2p+1}$;

p is an integer of from about 1 to about 10; and

is as defined in formula F';

d) substantially oxidizing said fluoroalkyl sulfide of step c with an oxidizing reagent to form a fluoroalkyl sulfone derivative having formula K';

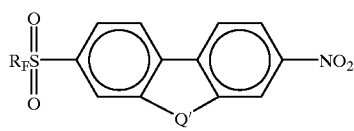

K' wherein $R_F$, p, and

are as previously defined in formula L';

e) further reacting the fluoroalkyl sulfone derivative of step d with a nucleophilic reagent in the presence of an aprotic solvent to form a compound having formula M'

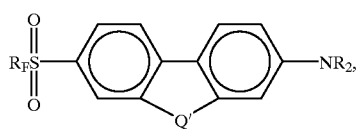

M' said compound having formula M' further having a 9-carbonyl, wherein

R is selected from the group consisting of phenyl, naphthyl, and a straight, branched and cyclic aliphatic alkyl group having from about 1 to about 10 carbon atoms; and $R_F$, p, and

are as previously defined in formula L';

f) deprotecting said 9-carbonyl of said 2,7-disubstituted fluoren-9-one derivative of step e in the presence of the acid catalyst of step a and active aromatic compounds and under conditions sufficient to yield a 2,7-disubstituted fluorenyl compound geminately alkylated at the 9-carbon, as shown in the formula G':

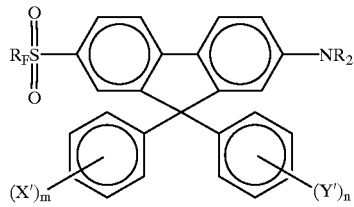

G' wherein
m and n are independently from about 1 to about 4;
X' and Y' are independently selected from the group consisting of —H, —$NH_2$, —$NR_2$, —NHR, —OH, —SR, —OR and —SH;

said active aromatics are

wherein H is —$NH_2$, —NHR, —$NR_2$, —OH, —OR, —SH, and —SR, and h is an integer of from about 1 to about 4;
R is as previously defined in formula M'; and
$R_F$ and p are as previously defined in formula L'; and g) optionally alkylating the compound having formula G' to form a compound having formula H':

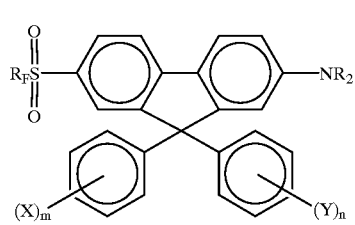

H' wherein
m and n are independently from about 1 to about 4;
R is as previously defined in formula M'; and
X and Y are groups capable of partaking in polymerization reactions and are independently selected from the group consisting of —H, —$NH_2$, —NHR, —$NR_2$, —OH, —OR, —SH, —SR, —COOH, —NCO,

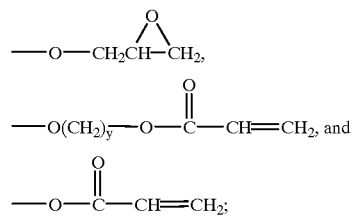

wherein y is about 1 to about 10;
in order to obtain an unsymmetrically substituted fluorenyl compound having formula H' having at least one X or Y group selected from the group consisting of —COOH, —NCO,

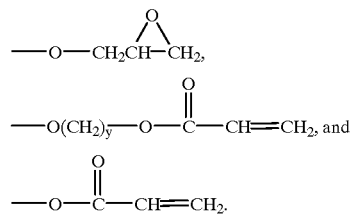

2. The process of claim 1 wherein said acid catalyst used in the deprotection reaction is present in an amount of from about 1% to about 5% based upon the total moles of the compound having formula M' used.

* * * * *